(12) United States Patent
Ichikawa et al.

(10) Patent No.: US 10,271,944 B2
(45) Date of Patent: Apr. 30, 2019

(54) INTRAOCULARLY-MOUNTED OBJECT AND INTRAOCULARLY-MOUNTED OBJECT HOLDING MEMBER

(71) Applicant: CHUKYO MEDICAL CO., INC., Nagoya-shi, Aichi (JP)

(72) Inventors: Kazuo Ichikawa, Nagoya (JP); Norihiko Yoshida, Nagoya (JP)

(73) Assignee: CHUKYO MEDICAL CO., INC., Nagoya-shi, Aichi (JP)

( * ) Notice: Subject to any disclaimer, the term of this patent is extended or adjusted under 35 U.S.C. 154(b) by 0 days.

(21) Appl. No.: 15/739,326

(22) PCT Filed: Jun. 29, 2016

(86) PCT No.: PCT/JP2016/069228
§ 371 (c)(1),
(2) Date: Dec. 22, 2017

(87) PCT Pub. No.: WO2017/018118
PCT Pub. Date: Feb. 2, 2017

(65) Prior Publication Data
US 2018/0185138 A1    Jul. 5, 2018

(30) Foreign Application Priority Data

Jul. 27, 2015 (JP) ................................. 2015-147498

(51) Int. Cl.
*A61F 2/16* (2006.01)
(52) U.S. Cl.
CPC .............. *A61F 2/16* (2013.01); *A61F 2/1608* (2015.04); *A61F 2/1629* (2013.01);
(Continued)

(58) Field of Classification Search
CPC ............ A61F 2/1608; A61F 2002/1699; A61F 2002/16903; A61F 2220/0016; A61F 2/1629; A61F 2002/1682
See application file for complete search history.

(56) References Cited

U.S. PATENT DOCUMENTS 5,769,890 A * 6/1998 McDonald ............ A61F 2/1602
606/107
2013/0116781 A1* 5/2013 Ben Nun .............. A61F 2/1635
623/6.43

(Continued)

FOREIGN PATENT DOCUMENTS

JP      2011-245322 A      12/2011
JP      2013123616 A  *   6/2013
WO      03/017873 A1       3/2003

OTHER PUBLICATIONS

The Office Action dated Jun. 28, 2016 for the corresponding Japanese Application JP2015-147498.

*Primary Examiner* — David H Willse
*Assistant Examiner* — Javier G Blanco
(74) *Attorney, Agent, or Firm* — Kenichiro Yoshida

(57) ABSTRACT

A hook portion 4 is provided which is formed so as to extend from base portions 21a of the ciliary processes 21 along the outer surfaces of the ciliary processes 21 via anterior end portions 21b of the ciliary processes 21 to base portions 21c at the opposite side. A leg portion 3 extending from the hook portion 4 toward the visual axis C is connected to the hook portion 4, and a lens 2 to be mounted in the eye of the patient is supported by the leg portion 3. The lens 2 is held in the eye of the patient in a state where the hook portion 4 is hooked or fitted to the ciliary processes 21.

7 Claims, 14 Drawing Sheets

(52) U.S. Cl.
CPC ..... *A61F 2/1664* (2013.01); *A61F 2002/1681* (2013.01); *A61F 2002/1682* (2015.04); *A61F 2002/1699* (2015.04); *A61F 2002/16903* (2015.04); *A61F 2220/0016* (2013.01)

(56) References Cited

U.S. PATENT DOCUMENTS

2013/0304206 A1\* 11/2013 Pallikaris .............. A61F 2/1651
                                                        623/6.43
2017/0312071 A1\* 11/2017 Ghabra ................ A61F 2/1629

\* cited by examiner

INTRAOCULARLY-MOUNTED OBJECT AND INTRAOCULARLY-MOUNTED OBJECT HOLDING MEMBER

CROSS-REFERENCE TO RELATED APPLICATIONS

This present application is a National Stage entry of International Application No. PCT/JP2016/069228, filed Jun. 29, 2016, which claims priority to Japanese Patent Application No. 2015-147498, filed Jul. 27, 2015, which issued as Japanese Patent No. 6023283 on Oct. 14, 2016. The disclosures of the prior applications are incorporated in their entirety reference.

FIELD OF THE INVENTION

The invention relates to an intraocularly-mounted object and an intraocularly-mounted object holding member.

BACKGROUND OF THE INVENTION

For example, as a method for treating a cataract, a treatment method is known in which a clouded crystalline lens of a patient is extracted and then an intraocular lens is mounted in the eye of the patient. When an intraocular lens is used in place of a crystalline lens the focus of which is adjustable by relaxation/contraction of ciliary muscle in the eye, it is an important issue how a visual target is brought into focus by the intraocular lens. Patent Document 1 discloses an intraocular lens that focuses on a visual target by using movement of an anterior capsule and a posterior capsule that are left when a crystalline lens is extracted and that move in response to relaxation/contraction of ciliary muscle.

CITATION LIST

Patent Document

Patent Document 1: Japanese Laid-Open Patent Publication No. 2011-245322

SUMMARY OF INVENTION

Problems to be Solved by the Invention

However, in the intraocular lens of Patent Document 1, a lens is held in the eye in a state where leg portions extending from the lens are fixed outside a sclera. Thus, relaxation/contraction movement of the ciliary muscle is hardly transmitted from the leg portions to the lens, and the lens moves indirectly via the capsules (the anterior capsule, the posterior capsule), which move in response to relaxation/contraction of ciliary muscle.

An object of the invention is to provide an intraocularly-mounted object and an intraocularly-mounted object holding member that are allowed to move directly in conjunction with relaxation/contraction movement of ciliary muscle.

Solution to the Problems and Effects of the Invention

An intraocularly-mounted object according to the invention includes:

a hook portion extending from a base portion of a ciliary process projecting from a ciliary body located in a circumferential direction about a visual axis toward the visual axis, along an outer surface of the ciliary process via an anterior end portion of the ciliary process to the base portion at an opposite side;

a leg portion extending from the hook portion toward the visual axis; and a to-be-mounted object supported by the leg portion and mounted in an eye, wherein the to-be-mounted object is held in the eye in a state where the hook portion is hooked or fitted to the ciliary process.

In the intraocularly-mounted object according to the invention, the to-be-mounted object supported by the leg portion extending from the hook portion is held in the eye in a state where the hook portion is hooked or fitted along the outer surface of the ciliary process, which moves in response to relaxation/contraction movement of ciliary muscle. Thus, relaxation/contraction movement of the ciliary muscle is transmitted through the leg portion, which extends from the hook portion, directly to the to-be-mounted object, so that it is possible to cause the to-be-mounted object to move directly in response to relaxation/contraction of the ciliary muscle. In the present specification, the "hook" means a bent shape, and the material thereof is not limited to metal.

An intraocularly-mounted object holding member according to the invention is an intraocularly-mounted object holding member to be connected to a leg portion supporting a to-be-mounted object mounted in an eye and hold the to-be-mounted object in the eye, the intraocularly-mounted object holding member including a hook portion extending from a base portion of a ciliary process projecting from a ciliary body located in a circumferential direction about a visual axis toward the visual axis, along an outer surface of the ciliary process via an anterior end portion of the ciliary process to the base portion at an opposite side, wherein the to-be-mounted object is held in the eye in a state where the hook portion is hooked or fitted to the ciliary process.

The invention is configured as an intraocularly-mounted object holding member (the aforementioned invention is configured as an intraocularly-mounted object). Similarly to the aforementioned invention of the intraocularly-mounted object, relaxation/contraction movement of the ciliary muscle is transmitted from the hook portion through the leg portion directly to the to-be-mounted object, so that the to-be-mounted object can be held such that the to-be-mounted object mounted in the eye moves directly in conjunction with relaxation/contraction of the ciliary muscle.

In an embodiment of the invention, the hook portion in the above intraocularly-mounted object and the above intraocularly-mounted object holding member includes:

a plurality of unit hook portions formed adjacently around the visual axis so as to extend along the ciliary process from the base portion via the anterior end portion to the base portion at the opposite side; and a connection portion connecting the plurality of adjacent unit hook portions.

According to this, the plurality of unit hook portions disposed adjacently around the visual axis are connected, and the number of locations at which the hook portion is hooked or fitted to the ciliary process is increased by the plurality of unit hook portions. Thus, the hook portion becomes easily hooked or fitted to the ciliary process. In addition, when the hook portion is hooked or fitted to the ciliary process, it is possible to stably hold the to-be-mounted object in the eye.

In an embodiment of the invention, the connection portion connects the plurality of adjacent unit hook portions in a comb shape or a net shape. Thus, the strength of the hook portion can be enhanced.

DESCRIPTION OF EMBODIMENTS

Figure 1A:
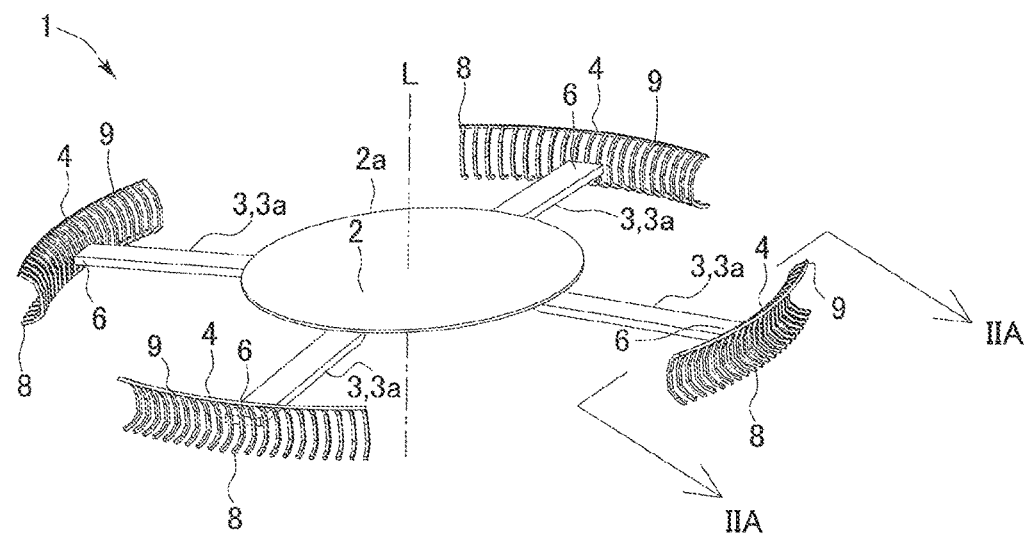
FIG. 1A is a schematic perspective view showing an intraocular lens (Embodiment 1) that is an intraocularly-mounted object according to the invention.
Figure 1B:
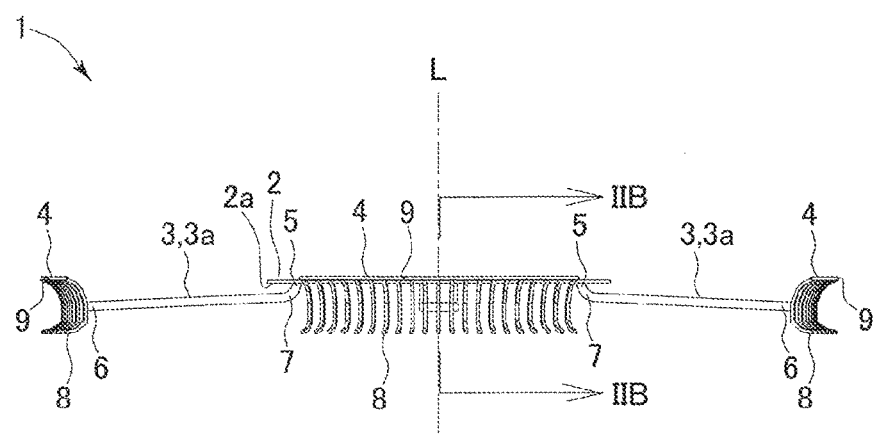
FIG. 1B is a schematic front view of the intraocular lens in FIG. 1A.
Figure 1C:
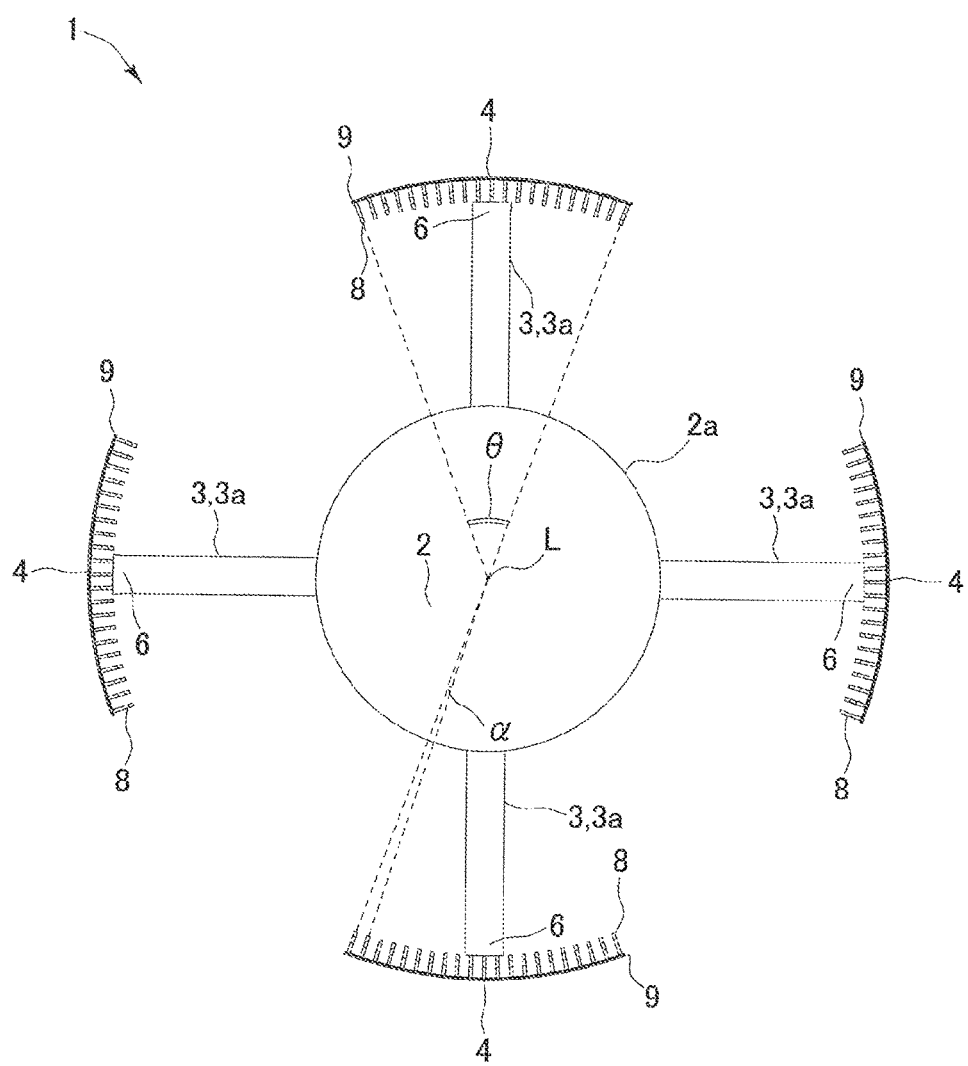
FIG. 1C is a schematic plan view of the intraocular lens in FIG. 1A.

FIGS. 1A to 1C show an intraocular lens 1 that is an example (Embodiment 1) of the invention (intraocularly-mounted object). The intraocular lens 1 is an artificial crystalline lens to be mounted in an eye of a patient with a cataract in place of a crystalline lens extracted from the patient, and each portion thereof is elastically deformable. As shown in FIG. 1A, the intraocular lens 1 includes a lens 2, a leg portion 3 extending from the lens 2, and hook portions 4 located at ends of the leg portion 3.

The lens 2 has elasticity and is formed in a disc shape. The lens 2 performs a lens function for a crystalline lens (for example, a clouded crystalline lens) extracted from a patient with a cataract. In FIG. 1A, reference character L represents a perpendicular axial line L passing through the center of a front surface of the lens 2 and is shown for the sake of convenience.

The lens 2 is supported by the leg portion 3. The leg portion 3 has a plurality of (four in Embodiment 1) legs 3$a$ that support the lens 2. The respective legs 3$a$ extend in the lateral direction of the lens 2 (in a direction away from the axial line L) from a plurality of locations in the circumferential direction of the lens 2 (a plurality of locations on an outer peripheral portion 2$a$ of a back surface of the lens 2). As shown in FIG. 1B, each leg 3$a$ has one end portion 5 located close to the lens 2, another end portion 6 located far from the lens 2, and a bent portion 7 that is located between the one end portion 5 and the other end portion 6 and at which the direction in which the leg 3$a$ extends is changed.

The one end portion 5 is a base point of the leg 3$a$ that is located on the outer peripheral portion 2$a$ of the back surface of the lens 2 (a part of the outer peripheral portion 2$a$) and that extends from the lens 2. The other end portion 6 is a termination portion of the leg 3$a$ that extends in the lateral direction of the lens 2 from the one end portion 5. The bent portion 7 is located at the one end portion 5 side, and curves and directs the leg 3$a$ extending obliquely downward from the back surface of the lens 2 so as to be away from the axial line L, toward the outer side of the lens 2.

The leg portion 3 is produced from a material having elasticity, for example, an elastomer resin. The leg portion 3 is formed separately from the lens 2, and is joined to the lens 2 by a known method (for example, bonding with a contact material).

As shown in FIG. 1C, a hook portion 4 is provided at the other end portion 6 of each leg 3$a$. A plurality of the hook portions 4 are discontinuously disposed around the axial line L (four hook portions 4 are disposed at regular intervals around the axial line L). Each hook portion 4 includes a plurality of unit hook portions 8 (see FIGS. 2A and 2B) each formed in a substantially C claw-like shape so as to project toward a central portion of the lens 2 (the axial line L), and a connection portion 9 connecting the plurality of unit hook portions 8.

Figure 2A:
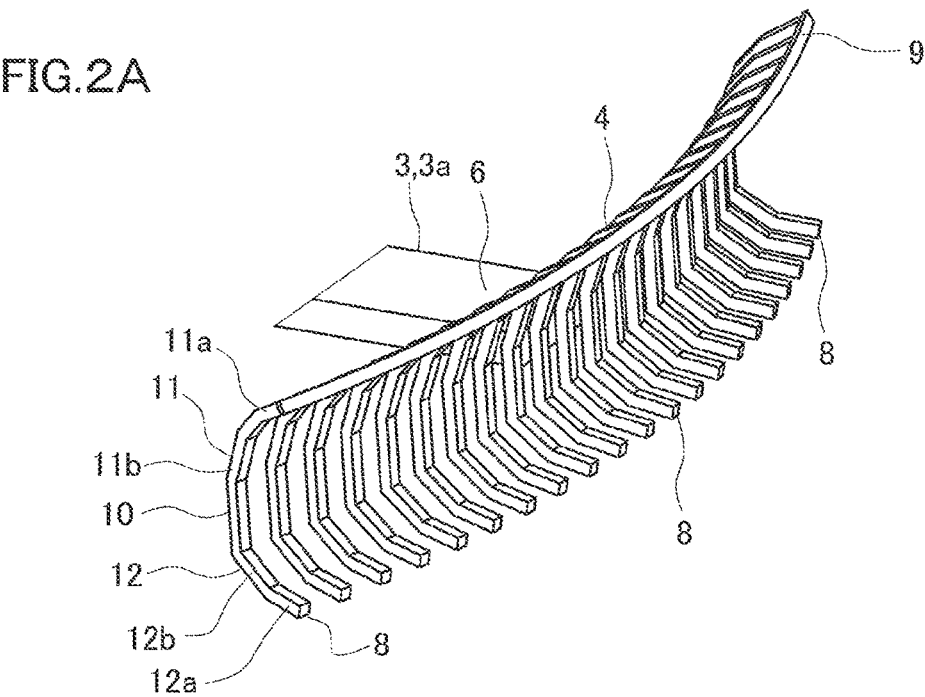
FIG. 2A is an IIA-IIA enlarged view of FIG. 1A.
Figure 2B:
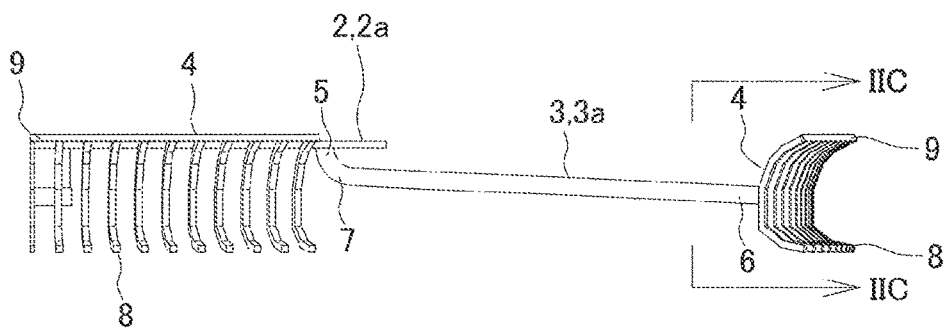
FIG. 2B is an IIB-IIB enlarged view of FIG. 1B.
Figure 2C:
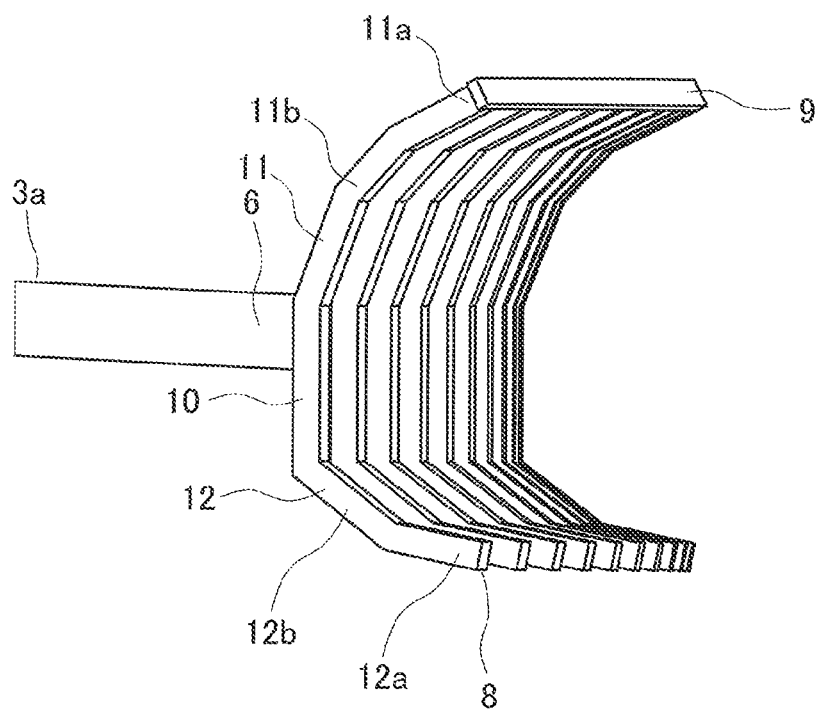
FIG. 2C is an IIC-IIC enlarged view of FIG. 2B.

As shown in FIG. 2C, each substantially-C-shaped unit hook portion 8 has an intermediate portion 10, an upper portion 11, and a lower portion 12. The intermediate portion 10 extends in the thickness direction of the lens 2 (the up-down direction in the drawing). The upper portion 11 extends obliquely upward from the upper end of the intermediate portion 10 so as to be away from the lens 2 (the left side in the drawing), and includes an upper bent portion 11b that sharply bends at a position between an end portion close to the lens 2 (at the left side in the drawing) and an end portion 11a far from the lens 2. The lower portion 12 extends obliquely downward from the lower end of the intermediate portion 10 so as to be away from the lens 2 (the left side in the drawing), and includes a lower bend portion 12b that sharply bends at a position between an end portion close to the lens 2 (at the left side in the drawing) and an end portion 12a far from the lens 2.

Figure 2D:
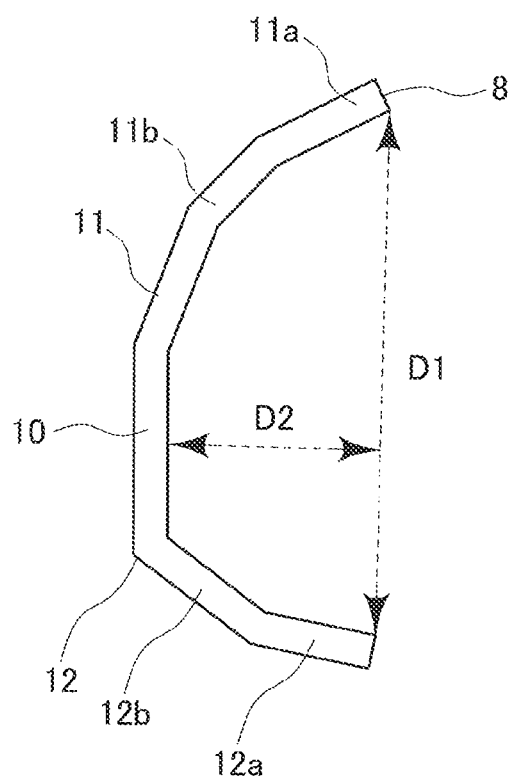
FIG. 2D is a schematic front view showing one unit hook portion in FIG. 2C.

As shown in FIG. 2D, in each substantially-C-shaped unit hook portion 8, a length (a straight line D1) obtained by connecting the end portion 11a of the upper portion 11 and the end portion 12a of the lower portion 12 at the shortest distance is preferably within the range of 1 mm to 4 mm. The maximum length of a perpendicular line (a straight line D2) extending from the intermediate portion 10 to the straight line D1 is preferably within the range of 0.5 mm to 2 mm. Furthermore, the ratio between the straight line D1 and the straight line D2 is preferably between 2:1 and 8:1.

Referring back to FIG. 1C, the plurality of unit hook portions 8 are disposed adjacently at regular intervals over the range of an acute angle θ around the axial line L. The adjacent unit hook portions 8 are preferably disposed at every angle α (for example, 1 degree to 9 degrees) around the axial line L.

The plurality of unit hook portions 8 disposed adjacently are connected by the connection portion 9. The connection portion 9 is located so as to connect the end portions 11a (see FIG. 2C) of the plurality of unit hook portions 8 disposed adjacently over the range of the acute angle θ around the axial line L. Thus, as shown in FIG. 2A, the hook portion 4 as a whole is formed in a comb shape.

The hook portion 4 (the unit hook portions 8 and the connection portion 9) is produced from a material having elasticity, for example, an elastomer resin. The hook portion 4 and the leg portion 3 may be formed so as to be integrated with each other, or the hook portion 4 and the leg portion 3 may be formed separately and then joined to each other by a known method (for example, bonding with a contact material).

The intraocular lens 1 having the above configuration is mounted in an eye of a patient with a cataract in place of the crystalline lens of the patient. Hereinafter, flow of a series of actions for a doctor to mount the intraocular lens 1 in an eye of a patient will be described. In Embodiment 1, an example in which the doctor mounts the intraocular lens 1 in the eye of the patient from which the crystalline lens is fully extracted (the capsules are also extracted) will be described.

Figure 3A:
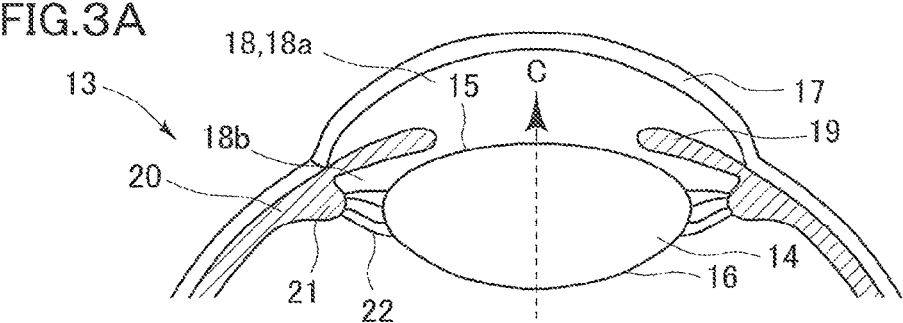
FIG. 3A is a schematic cross-sectional view schematically showing the interior of an eye of a patient before a crystalline lens is extracted.

FIG. 3A schematically shows an eye 13 of a patient, and a state before a crystalline lens 14 of the patient with a cataract is extracted therein. In Embodiment 1, the crystalline lens 14 of the patient who has a cataract is extracted together with an anterior capsule 15 and a posterior capsule 16. In FIG. 3A, an iris 19 located within an eye chamber 18 (between an anterior chamber 18a and a posterior chamber 18b) behind a cornea 17 (at the lower side in the drawing) is opened by a drug. A ciliary body 20 (ciliary muscle) is located in a circumferential direction about a visual axis C of the patient (the ciliary body 20 is annularly located), and ciliary processes 21 project from the ciliary body 20 toward the visual axis C and are connected to the crystalline lens 14 by a ciliary zonule 22.

Figure 3B:
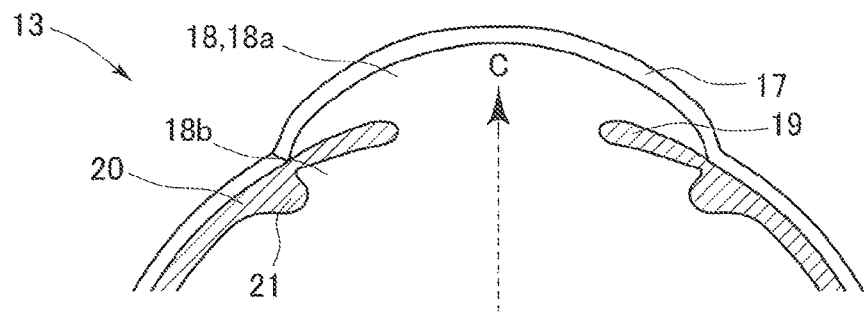
FIG. 3B is a schematic cross-sectional view showing a state where the crystalline lens is fully extracted from the interior of the eye in FIG. 3A.
Figure 3C:
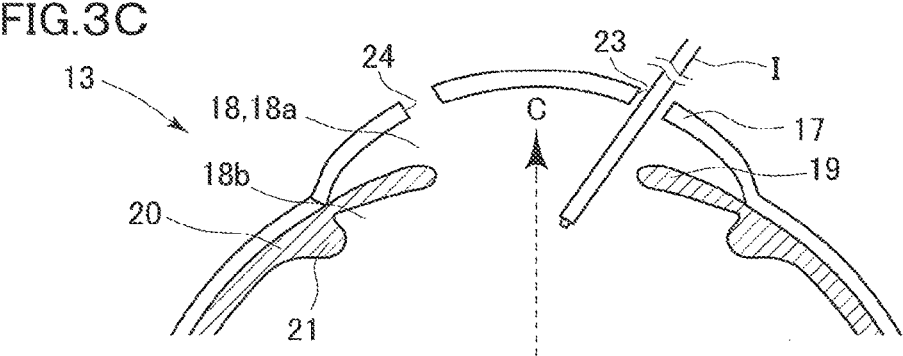
FIG. 3C is a schematic cross-sectional view showing a state where an insertion tool is inserted into the eye in FIG. 3B.

The doctor extracts the entireties of the crystalline lens 14 (FIG. 3A) and the ciliary zonule 22 of the patient by a known method (FIG. 3B). Thereafter, as shown in FIG. 3C, the doctor incises a part of the cornea 17 to form an insertion hole 23 through which an end portion of an insertion tool I for inserting the intraocular lens 1 into the eye is inserted into the eye. In addition, the doctor also forms an insertion hole 24 through which a pair of forceps (not shown) for operating the intraocular lens 1 inserted in the eye is inserted into the eye.

The elastically deformable intraocular lens 1 is stored in the insertion tool I, which is inserted into the eye, in a state where the intraocular lens 1 is rolled into a tubular shape. The doctor inserts the end of the insertion tool I having the intraocular lens 1 stored therein, through the insertion hole 23, causes the end to reach the posterior chamber 18b, and discharges the intraocular lens 1 through the end of the insertion tool I into the posterior chamber 18b.

Separately, the doctor inserts the pair of forceps (not shown) through the insertion hole 24 into the eye, pinches the leg 3a (see FIG. 1A) of the intraocular lens 1 discharged into the eye, and draws the hook portion 4 provided at the other end portion 6 of the leg 3a, to the ciliary processes 21. Next, the doctor presses the hook portion 4 (the plurality of adjacent unit hook portions 8) against the ciliary processes 21 so as to squeeze the ciliary processes 21 into the space between the upper portions 11 and the lower portions 12 of the substantially-C-shaped unit hook portions 8 (see FIG. 2C). When the ciliary processes 21 are squeezed into the space between the upper portions 11 and the lower portions 12, the unit hook portions 8 become elastically deformed such that the space between the upper portions 11 and the lower portions 12 widens. The doctor confirms that the ciliary processes 21 have been squeezed into the space between the upper portions 11 and the lower portions 12, and separates the leg 3a pinched by the pair of forceps, from the pair of forceps.

Accordingly, the force that widens the space between the upper portions 11 and the lower portions 12 is released, so that the space between the upper portions 11 and the lower portions 12 becomes narrow (see arrows in FIG. 3E) and the unit hook portions 8 become fitted to the ciliary processes 21. That is, by pressing the hook portion 4 against the ciliary processes 21, it becomes possible to fit the plurality of adjacent unit hook portions 8 to the ciliary processes 21 at one time. If the unit hook portions 8 fail to become fitted to the ciliary processes 21, the unit hook portions 8 may be individually fitted to the ciliary processes 21 by using the pair of forceps.

Figure 3D:
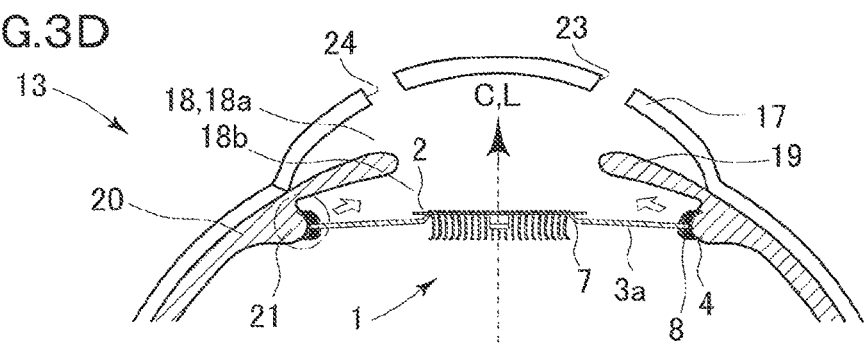
FIG. 3D is a schematic cross-sectional view showing state where the intraocular lens in FIG. 1A is mounted in the eye of the patient subsequently to FIG. 3C.

After the hook portion 4 is fitted to the ciliary processes 21, the doctor performs the same operation on the hook portions 4 provided at the remaining three legs 3a, whereby the intraocular lens 1 is held in the eye by the hook portions 4. In a state where the intraocular lens 1 is held in the eye by the hook portions 4 as shown in FIG. 3D, the lens 2 is located in the posterior chamber 18b such that the axial line L of the lens 2 coincides with the visual axis C of the eye of the patient. Thereafter, the doctor takes the pair of forceps, etc. out of the eyeball, and mounting the intraocular lens 1 to the patient with the cataract is completed.

Figure 3E:
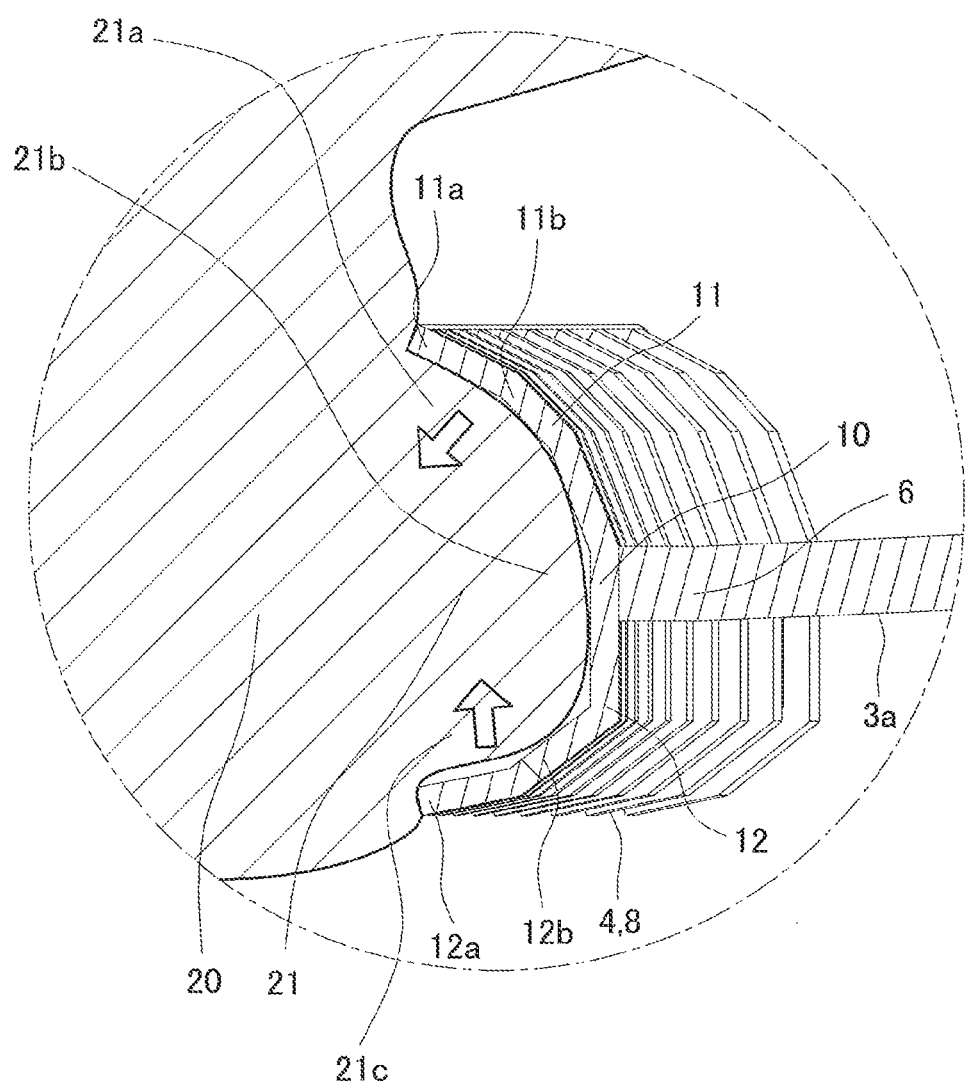
FIG. 3E is a partially enlarged view of FIG. 3D.

In a state where the hook portion 4 (the unit hook portions 8) is attached to the ciliary processes 21 as shown in FIG. 3E, the hook portion 4 extends from base portions 21a of the ciliary processes 21 along the outer surfaces of the ciliary processes 21 via anterior end portions 21b of the ciliary processes 21 to base portions 21c at the opposite side. When the patient having the intraocular lens 1 mounted therein attempts to focus on a visual target (a target that the patient attempts to see), the ciliary body 20 relaxes or contracts in accordance with the position of the visual target.

According to the finding by the inventors, in response to relaxation/contraction of the ciliary body 20, the ciliary processes 21 move toward the visual axis C, for example, toward the obliquely upper side as shown by arrows in FIG. 3D, and the hook portions 4 attached to the ciliary processes 21 move in conjunction therewith.

By the hook portions 4 moving obliquely upward, the lens 2 also moves upward. Furthermore, since the legs 3a, which connect the hook portions 4 and the lens 2, have elasticity, when the hook portions 4 move obliquely upward toward the visual axis C, the bent portions 7 are pressed toward the visual axis C, and the one end portion 5 of each leg 3a is changed into an attitude in which the one end portion 5 is nearly orthogonal to the lens 2. Thus, when the hook portions 4 move obliquely upward toward the visual axis C, the lens 2 is pressed upward. Meanwhile, when the hook portions 4 that have moved obliquely upward toward the visual axis C return to the original positions, the lens 2 moves downward and returns to the original position. By the lens 2 moving up and down, the distance between the lens 2 and the visual target an image of which is to be formed on the retina by the lens 2 is changed. Thus, the patient having the intraocular lens 1 mounted therein is allowed to adjust the focus to the visual target.

In Embodiment 1, the example in which only the intraocular lens 1 is mounted in the eye has been described. However, when another lens is additionally inserted to the anterior or posterior side of the intraocular lens 1 in the eye, it is also possible to adjust the focal distance of a pair of the lenses.

As described above, the intraocular lens 1 is held in the eye by the hook portions 4, and the hook portions 4 are fitted so as to extend along the outer surfaces of the ciliary processes 21, which move in response to relaxation/contraction movement of the ciliary body 20. Thus, relaxation/contraction movement of the ciliary body 20 is transmitted from the hook portions 4 through the legs 3a directly to the lens 2, so that it is possible to cause the lens 2 (the intraocular lens 1) to move directly in response to relaxation/contraction of the ciliary body 20.

As shown in FIG. 2A, each hook portion 4 includes the plurality of unit hook portions 8 and the connection portion 9 connecting the unit hook portions 8. The unit hook portions 8 extend along the ciliary processes 21 from the base portions 21a via the anterior end portions 21b to the base portions 21c at the opposite side as shown in FIG. 3E. As shown in FIG. 1C, the plurality of unit hook portions 8 are disposed adjacently around the axial line L (the visual axis C (see FIG. 3D)). Thus, the number of locations at which the hook portion 4 becomes fitted to the ciliary processes 21 is increased by the plurality of unit hook portions 8 disposed adjacently around the visual axis C (axial line L). In addition, since the plurality of unit hook portions 8 are disposed adjacently around the visual axis C, the hook portion 4 becomes easily fitted to the ciliary processes 21, which are annularly formed around the visual axis C. Thus, when each hook portion 4 becomes fitted to the ciliary processes 21, it becomes possible to stably hold the lens 2 in the eye.

As shown in FIG. 1A, the respective legs 3a, which support the lens 2, extend in the lateral direction of the lens 2 (the direction away from the axial line L) from the plurality of locations in the circumferential direction of the lens 2 (on the outer peripheral portion 2a). Thus, it becomes possible to stably support the lens 2 by the plurality of legs 3a located in the circumferential direction of the lens 2. Since each leg 3a having elasticity includes the bent portion 7 as shown in FIG. 1B, the bend of the bent portion 7 can be changed by external force.

As shown in FIG. 1C, the hook portions 4 provided at the other end portions 6 of the legs 3a are discontinuously formed (at regular angle intervals) around the axial line L. Thus, a region of each hook portion 4 that is fitted to the ciliary processes 21 is limited (the region of each hook portion 4 is reduced as compared to the case where the hook portions 4 are continuously formed around the axial line L), so that it becomes easy to mount the intraocular lens 1. Each hook portion 4 includes the plurality of unit hook portions 8 each formed in a substantially C claw-like shape (see FIG. 2A) so as to project toward the central portion of the lens 2 (the axial line L), and the connection portion 9 connecting the plurality of unit hook portions 8. Since each unit hook portion 8 has a substantially C shape, it becomes easy to squeeze the ciliary processes 21 into the inner portion surrounded by the substantially C shapes of the unit hook portions 8. In addition, sine each unit hook portion 8 is formed in a claw-like shape, the ciliary processes 21 become easily fitted to the unit hook portions 8.

As shown in FIG. 2C, each substantially-C-shaped unit hook portion 8 having elasticity includes the upper bent portion lib and the lower bend portion 12b. Thus, the sharp bending of the upper bent portion lib and the lower bend portion 12b can be changed by external force. When the straight line D1 of each unit hook portion 8 is within the range of 1 mm to 4 mm as shown in FIG. 2D, it becomes easy to squeeze the ciliary processes 21 into the internal region surrounded by the substantially C shapes of the unit hook portions 8. When the straight line D2 is within the range of 0.5 mm to 2 mm, the ciliary processes 21 squeezed into the internal region surrounded by the substantially C shapes of the unit hook portions 8 become less likely to be detached from the unit hook portions 8. Furthermore, when the ratio between the straight line D1 and the straight line D2 is between 2:1 and 8:1, it becomes easy to attach the unit hook portions 8 to the ciliary processes 21.

Referring back to FIG. 1C, the plurality of unit hook portions 8 are disposed adjacently over the range of the acute angle θ around the axial line L. Thus, since the unit hook portions 8 are disposed adjacently in an arc so as to correspond to the annularly-disposed ciliary processes 21, each unit hook portion 8 becomes easily fitted to the ciliary processes 21. In the case where the adjacent unit hook portions 8 are disposed at every angle α (for example, 1 degree to 9 degrees) around the axial line L, the intraocular lens 1 can be stably held when the ciliary processes 21 become fitted to the hook portions 4.

The connection portion 9 connecting the plurality of unit hook portions 8, which are disposed adjacently, connects the end portions 11a of the plurality of adjacent unit hook portions 8 as shown in FIG. 2C. Thus, the positions of the end portions 11a of the respective unit hook portions 8 are aligned by the connection portion 9, so that it becomes easy to squeeze the ciliary processes 21 into the internal portion of the hook portion 4 (the internal region of each substantially-C-shaped unit hook portion 8) in pressing the hook portion 4 against the ciliary processes 21. As shown in FIG. 2A, the hook portion 4 as a whole is formed in a comb shape. Thus, the end portion 12a of each unit hook portion 8 is not restricted by the connection portion 9, becomes elastically deformable, and thus can accommodate a difference in size among the ciliary processes 21. In addition, a plurality of locations at which the ciliary processes 21 become fitted can be ensured by the plurality of unit hook portions 8. Furthermore, the connection portion 9 connects the plurality of adjacent unit hook portions 8 in a comb shape and thus can enhance the strength of the hook portion 4.

As shown in FIG. 1C, similarly to the unit hook portions 8, the plurality of hook portions 4 are disposed around the axial line L. Thus, by the ciliary processes 21 becoming fitted to the plurality of hook portions 4 located around the axial line L, the intraocular lens 1 can be stably held in the eye.

Figure 4A:
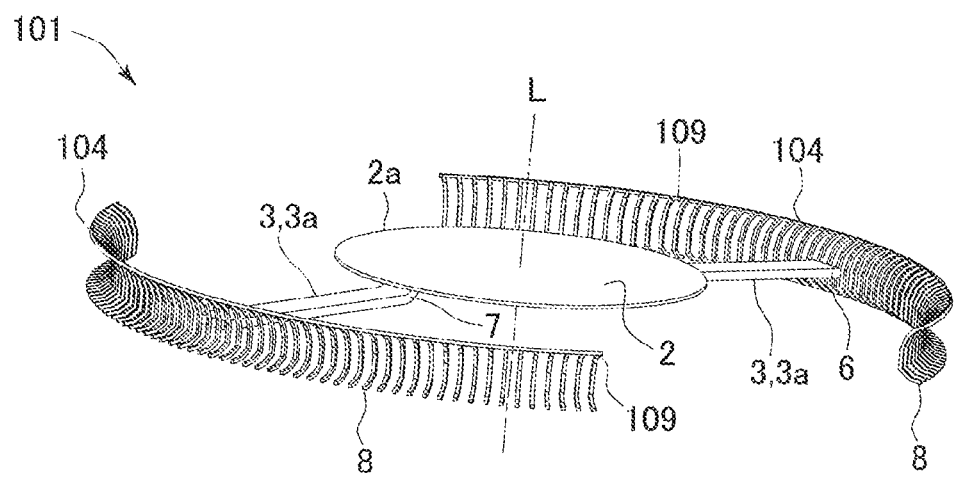
FIG. 4A is a schematic perspective view showing Modification 1 of FIG. 1A.

FIGS. 4A and 4B and FIGS. 5A to 5C show intraocular lenses 101, 201, and 301 showing Modifications 1 to 3 of the intraocular lens 1 of Embodiment 1. Hereinafter, the same components as those in Embodiment 1 are designated by the same reference characters, and the description thereof is omitted. As shown in FIG. 4A, the intraocular lens 101 has two legs 3a around the axial line L. A hook portion 104 is provided at the other end portion 6 of each leg 3a, and includes a plurality of unit hook portions 8 disposed adjacently at regular intervals over the range of an obtuse angle about the axial line L, and a connection portion 109 connecting the plurality of unit hook portions 8 at end portions 11a. The intraocular lens 101 is stably held in an eye by the plurality of unit hook portions 8 (hook portion 104) disposed so as to spread at the obtuse angle about the axial line L.

Figure 4B:
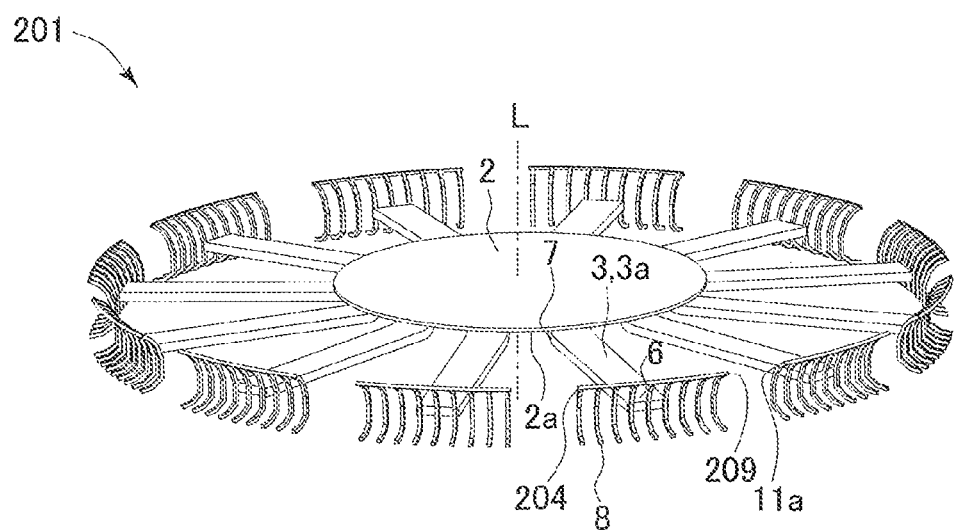
FIG. 4B is a schematic perspective view showing Modification 2 of FIG. 1A.

As shown in FIG. 4B, the intraocular lens 201 has a plurality of legs 3a disposed radially around the axial line L. A hook portion 204 is provided at the other end portion 6 of each leg 3a, and includes a plurality of unit hook portions 8 disposed adjacently at regular intervals over the range of an acute angle about the axial line L, and a connection portion 209 connecting the plurality of unit hook portions 8 at end portions 11a. Since the legs 3a are radially connected to the lens 2, it becomes possible to minutely transmit movement of the ciliary processes 21 located annually around the visual axis C (axial line L), through the hook portions 204 to the lens 2.

Figure 5A:
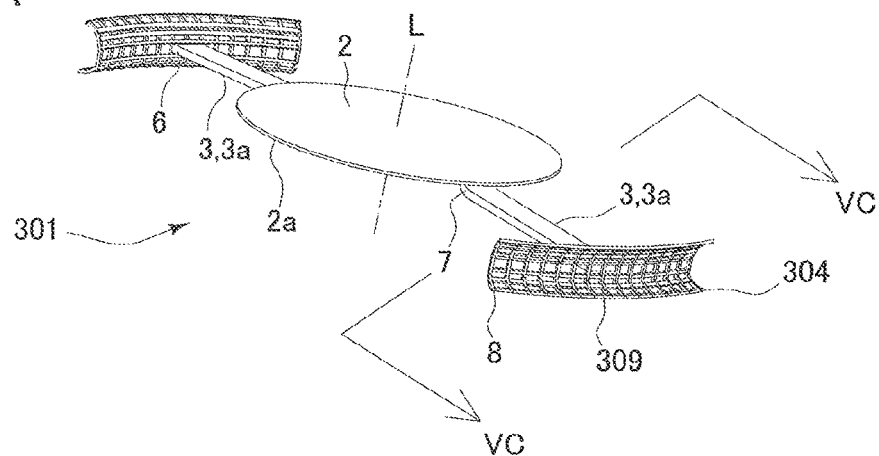
FIG. 5A is a schematic perspective view showing Modification 3 of FIG. 1A.
Figure 5B:
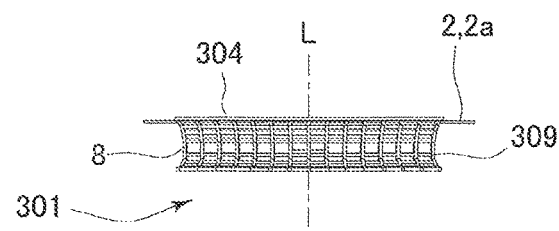
FIG. 5B is a schematic front view showing Modification 3 of FIG. 1A.
Figure 5C:
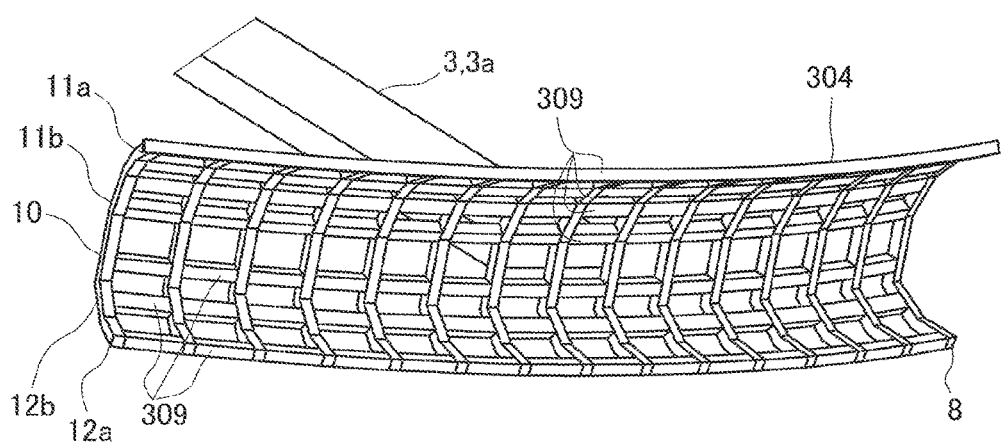
FIG. 5C is a VC-VC enlarged view of FIG. 5A.

As shown in FIGS. 5A to 5C, the intraocular lens 301 has two legs 3a around the axial line L. A hook portion 304 is provided at the other end portion 6 of each leg 3a, and includes a plurality of unit hook portions 8 disposed adjacently at regular intervals over the range of an acute angle about the axial line L, and a connection portion 309 connecting the plurality of unit hook portions 8 at end portions 11a. As shown in FIG. 5C, the connection portion 309 connects the end portions 11a and 12a, the bent portions 11b and 12b, and the intermediate portions 10 of the plurality of respective unit hook portions 8, so that the hook portion 304 as a whole is formed in a net shape. Thus, the strength of the hook portion 304 can be enhanced.

Embodiment 1 and Modifications 1 to 3, which are the intraocular lenses 1, 101, 201, and 301 each of which is to be mounted in the eye of the patient from which the crystalline lens 14 is fully extracted, have been describe above. In Embodiment 1, the example in which the crystalline lens 14 is fully extracted has been described. In Embodiment 2, an intraocular lens to be mounted in the eye of the patient from which the crystalline lens 14 is extracted such that a part of the anterior capsule 15 and the posterior capsule 16 are left, will be described.

Figure 6A:
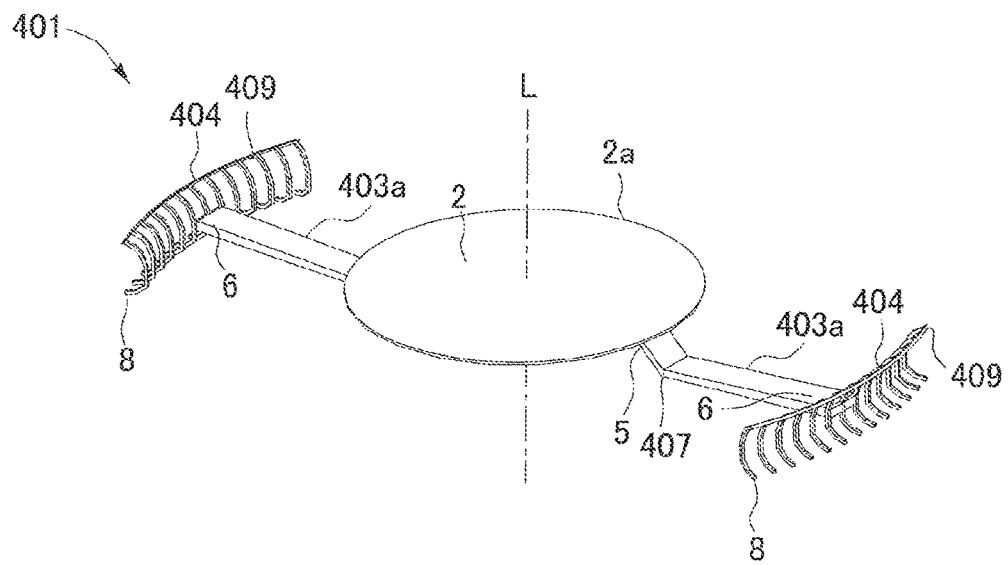
FIG. 6A is a schematic perspective view showing an intraocular lens (Embodiment 2) that is the intraocularly-mounted object according to the invention.
Figure 6B:
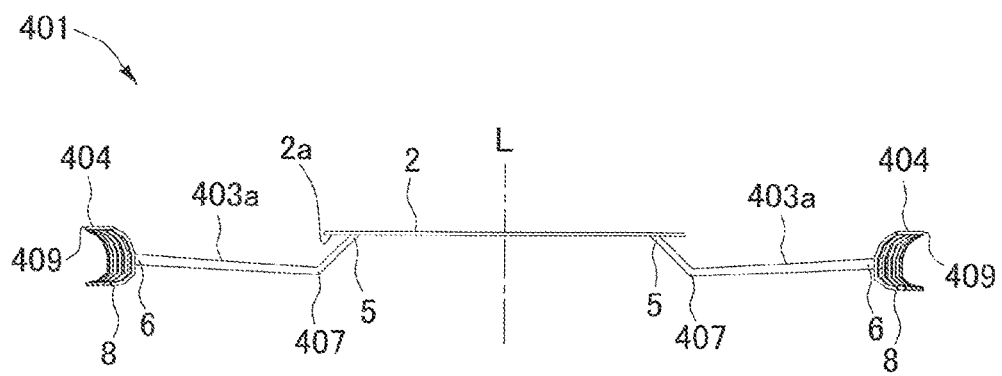
FIG. 6B is a schematic front view of the intraocular lens in FIG. 6A.
Figure 6C:
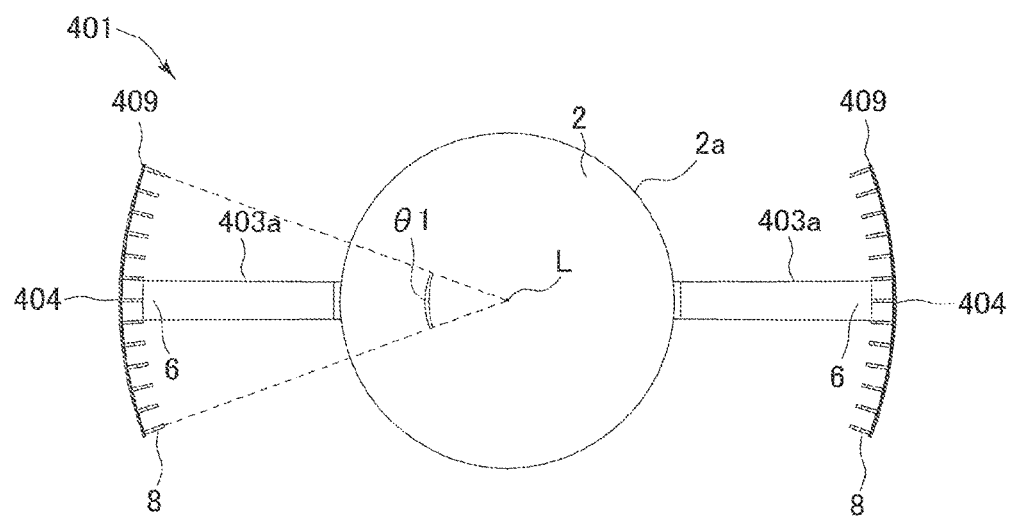
FIG. 6C is a schematic plan view of the intraocular lens in FIG. 6A.
Figure 6D:
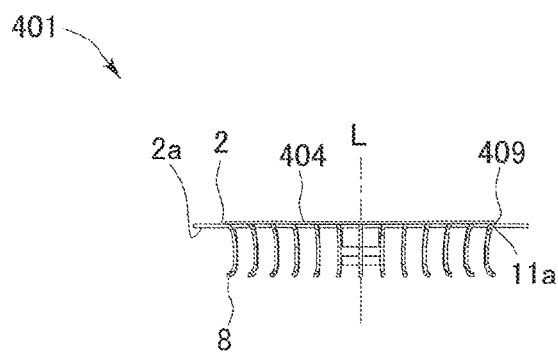
FIG. 6D is a schematic side view of the intraocular lens in FIG. 6A.

As shown in FIGS. 6A to 6D, an intraocular lens 401 of Embodiment 2 has two legs 403a around the axial line L. As shown in FIG. 6B, each leg 403a has a bent portion 407 that is located between one end portion 5 and another end portion 6 and that bends and directs the leg 403a extending obliquely downward from the back surface of the lens 2 so as to be away from the axial line L, toward the outer side of the lens 2. As shown in FIG. 6C, a hook portion 404 is provided at the one end portion 6 of each leg 403a, and includes a plurality of unit hook portions 8 disposed adjacently at regular intervals over the range of an acute angle θ1 around the axial line L, and a connection portion 409 connecting the plurality of unit hook portions 8 at end portions 11a (see FIG. 6D) of upper portions 11. As shown in FIG. 6A, the hook portion 404 as a whole is formed in a hoe shape.

Figure 7A:
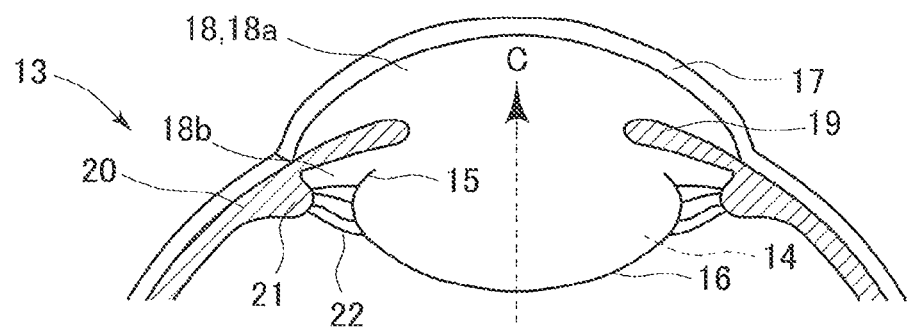
FIG. 7A is a schematic cross-sectional view schematically showing the interior of the eye of the patient from which the crystalline lens is extracted such that a part of an anterior capsule and a posterior capsule are left.
Figure 7B:
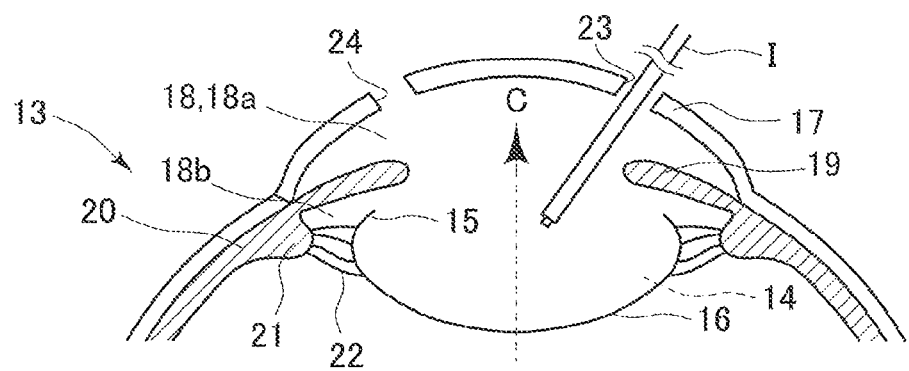
FIG. 7B is a schematic cross-sectional view showing a state where the insertion tool is inserted into the eye in FIG. 7A.

The intraocular lens 401 having the above configuration is mounted in an eye of a patient with a cataract in place of the crystalline lens of the patient. Hereinafter, flow of a series of actions for a doctor to mount the intraocular lens 401 in the eye of the patient will be described. The doctor extracts the crystalline lens 14 by a known method such that a part of the anterior capsule 15 and the posterior capsule 16 are left (FIG. 7A), and then forms insertion holes 23 and 24 in the cornea 17 as shown in FIG. 7B. Thereafter, the doctor inserts a scalpel (not shown) through the insertion hole 24, and forms slits (not shown) for taking the hook portions 404 (see FIG. 6A) of the intraocular lens 401 out of the capsule opposing the ciliary processes 21, in the capsule and at two locations corresponding to the hook portions 404.

Figure 7C:
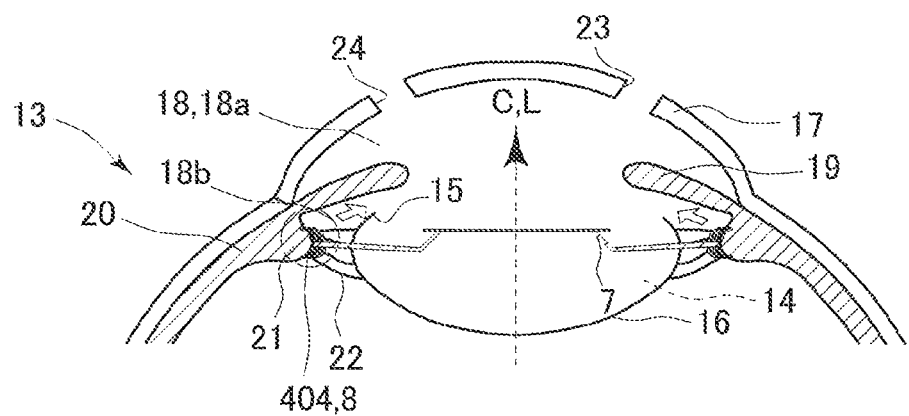
FIG. 7C is a schematic cross-sectional view showing a state where the intraocular lens in FIG. 6A is mounted in the eye of the patient subsequently to FIG. 7B.

The doctor inserts the end of the insertion tool I having the intraocular lens 401 stored therein, through the insertion hole 23, causes the end of the insertion tool I to reach the interior of the capsule (FIG. 7B), and then discharges the intraocular lens 401 through the end of the insertion tool I into the capsule. Separately, the doctor inserts a pair of forceps (not shown) through the insertion hole 24 into the eye, pinches the leg 403a of the intraocular lens 401 discharged into the eye, and takes the hook portion 404 out of the capsule through the slit (not shown). Next, the doctor presses the hook portion 404 against the ciliary processes 21 such that the ciliary processes 21 are forced toward the space between the upper portions 11 and the lower portions 12 (see FIG. 2A) of the substantially-C-shaped unit hook portions 8, thereby fitting the ciliary processes 21 to the hook portion 404. The doctor repeats the same operation on the other leg 403a, whereby the intraocular lens 401 is held in the eye (FIG. 7C). When the doctor hooks the hook portion 404 to the ciliary processes 21, if the ciliary zonule 22 obstructs the hook portion 404, the doctor may excise the obstructing ciliary zonule 22. When a hook portion having a connection portion connecting the plurality of unit hook portions 8 at the intermediate portions 10 is adopted, the connection portion is less likely to be obstructed by the ciliary zonule 22 in fitting the hook portion to the ciliary processes 21.

Figure 7D:
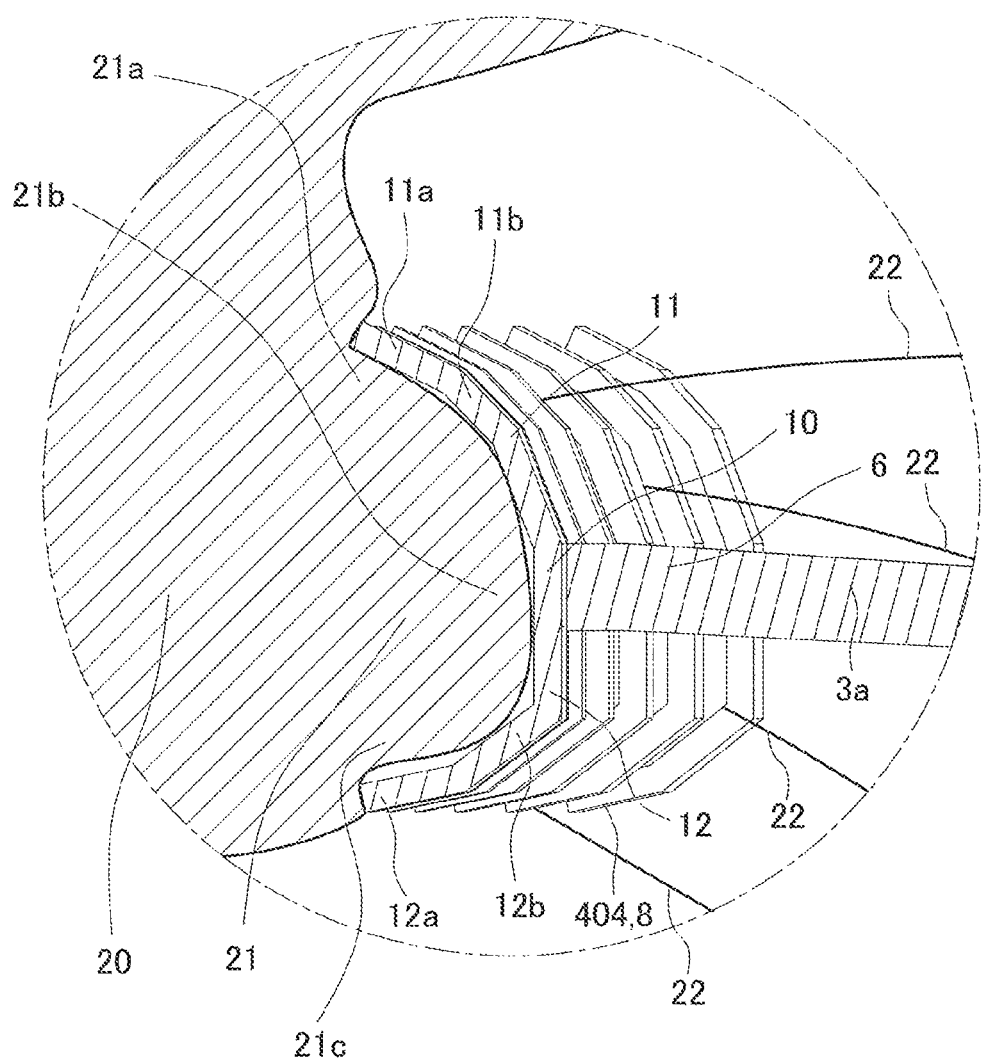
FIG. 7D is a partially enlarged view of FIG. 7C.

In a state where the hook portion 404 is attached to the ciliary processes 21 as shown in FIG. 7D, the ciliary zonule 22 extending from the ciliary processes 21 to the capsule is located in the gap between the adjacent unit hook portions 8. Thus, it is possible to attach the intraocular lens 401 to the ciliary processes 21 with the ciliary zonule 22 maintained.

As described above, the intraocular lens 401 is held in the eye by the hook portions 404. As shown in FIG. 7C, the hook portions 404 become fitted to the outer surfaces of the ciliary processes 21, which move in response to relaxation/contraction movement of the ciliary body 20, in a state where the part of the anterior capsule 15 and the posterior capsule 16 are left. Thus, it is possible to cause the lens 2 to move directly in response to relaxation/contraction of the ciliary body 20. Since the lens 2 is held in the capsule, it is not necessary to provide a receiver to be used when the lens 2 drops.

Since each leg 403a has the bent portion 407 as shown in FIG. 6B, when the bent portion 407 is pressed in the direction toward the lens 2, the one end portion 5 of the leg 403a is easily changed into an attitude in which the one end portion 5 is nearly orthogonal to the lens 2. Thus, the lens 2 easily moves back and forth in response to change of the bent portion 407.

Figure 8A:
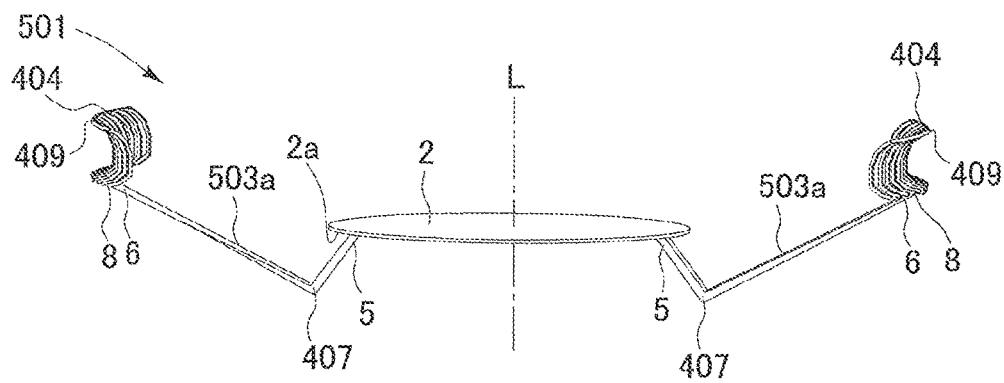
FIG. 8A is a schematic perspective view showing Modification 1 of FIG. 6A.
Figure 8B:
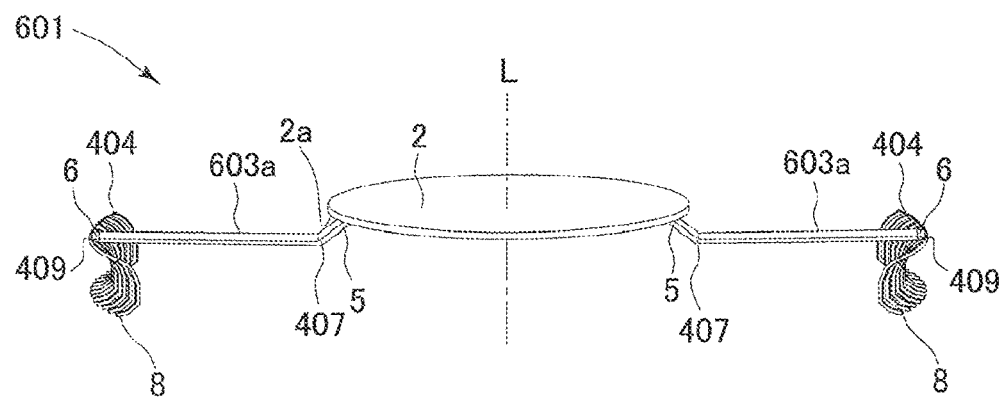
FIG. 8B is a schematic perspective view showing Modification 2 of FIG. 6A.
Figure 8C:
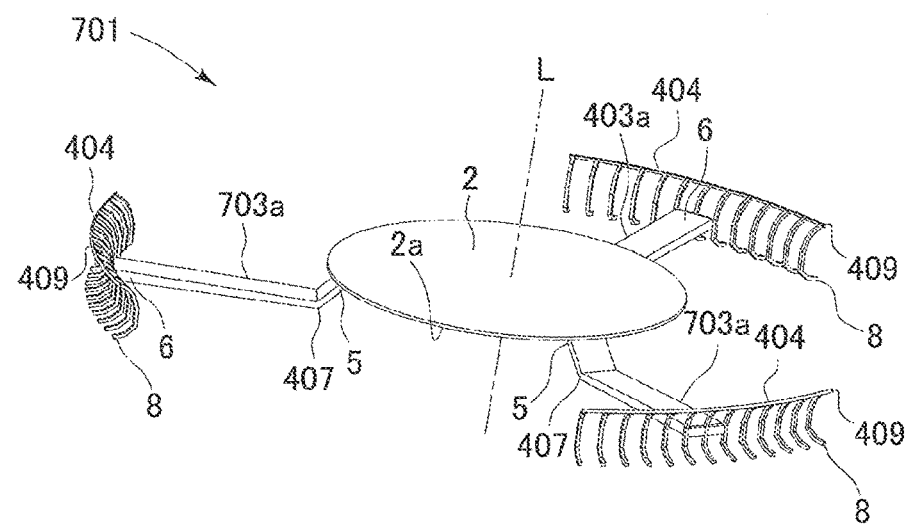
FIG. 8C is a schematic perspective view showing Modification 3 of FIG. 6A.

FIGS. 8A to 8C show intraocular lenses 501, 601, and 701 showing Modifications 4 to 6 of the intraocular lens 401 of the Embodiment 2. As shown in FIG. 8A, the intraocular lens 501 has two legs 503a around the axial line L. A hook portion 404 is provided at the other end portion 6 of each leg 503a. The other end portion 6 of each leg 503a is located at a lower end portion of the hook portion 404 (a portion corresponding to the end portions 12a of the lower portions 12 of the unit hook portions 8), and the one end portion 5 of each leg 503a is connected to the lens 2 such that the hook portion 404 is located higher than the front surface of the lens 2. Thus, the intraocular lens 501 can position the lens 2 at the eyeground side with respect to the ciliary processes 21.

As shown in FIG. 8B, the intraocular lens 601 has two legs 603a around the axial line L. A hook portion 404 is provided at the other end portion 6 of each leg 603a. The other end portion 6 of each leg 603a is located at an upper end portion of the hook portion 404 (a portion corresponding to the end portions 11a of the upper portions 11 of the unit hook portions 8), and the one end portion 5 of each leg 603a is connected to the lens 2 such that the hook portion 404 is located lower than the back surface of the lens 2. Thus, the intraocular lens 601 can position the lens 2 at the cornea 17 side (the side opposite to the eyeground) with respect to the ciliary processes 21.

As shown in FIG. 8C, the intraocular lens 701 has three legs 703a around the axial line L. The other end portion 6 of each leg 703a is located at an intermediate portion of a hook portion 404 (a portion corresponding to the intermediate portions 10 of the unit hook portions 8). Thus, the lens 2 can be stably held by the three hook portions 404 disposed at regular intervals around the axial line L.

In the above embodiments and modifications, the intraocular lens has been described as an example of the intraocularly-mounted object. However, the intraocularly-mounted object can be applied to various mounted objects to be mounted in an eye, such as a receiver which receives the dropped lens, in addition to the intraocular lens.

Figure 9A:
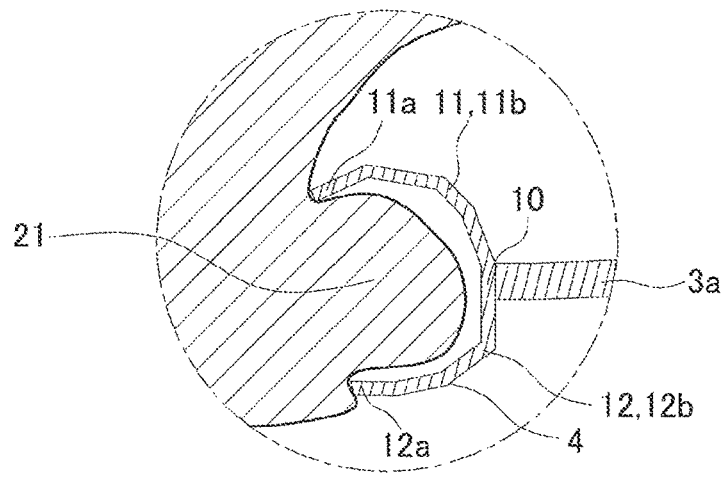
FIG. 9A is a cross-sectional view showing Modification 1 of a hook portion (unit hook portion).
Figure 9B:
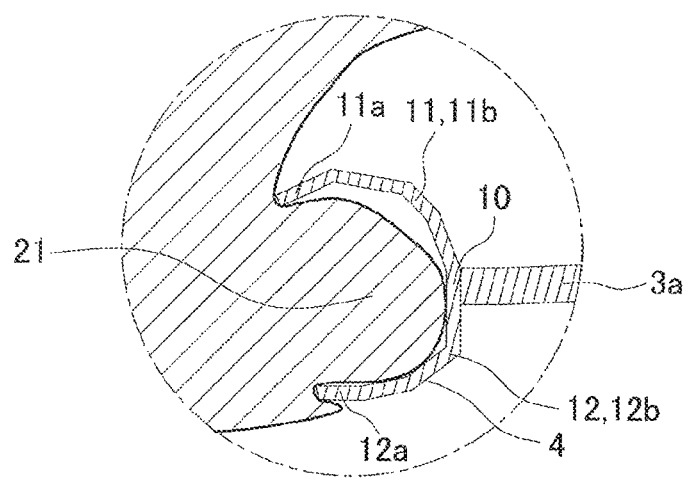
FIG. 9B is a cross-sectional view showing Modification 2 of the hook portion (unit hook portion).

In the above embodiments and modifications, the example in which the ciliary processes 21 are fitted to the hook portions 4 such that the unit hook portions 8 are in contact with the ciliary processes 21, has been described. However, the hook portions 4 do not necessarily need to be fitted to the ciliary processes 21. As shown in FIG. 9A, in a state where only the end portions 11a directing downward the upward-extending upper portions 11 and the end portions 12a directing upward the downward-extending lower portions 12 are in contact with the ciliary processes 21, the hook portions 4 may be hooked to the ciliary processes 21, whereby the lens 2 may be held in the eye. In addition, as shown in FIG. 9B, the intermediate portions 10 and the lower portions 12 may extend along the ciliary processes 21 so as to be in contact with the ciliary processes 21, and only the end portions 11a of the upper portions 11 may be hooked to the ciliary processes 21, whereby the lens 2 may be held in the eye. The to-be-mounted object only needs to be held in the eye in a state where each hook portions 4 is hooked or fitted to the ciliary processes 21.

Figure 9C:
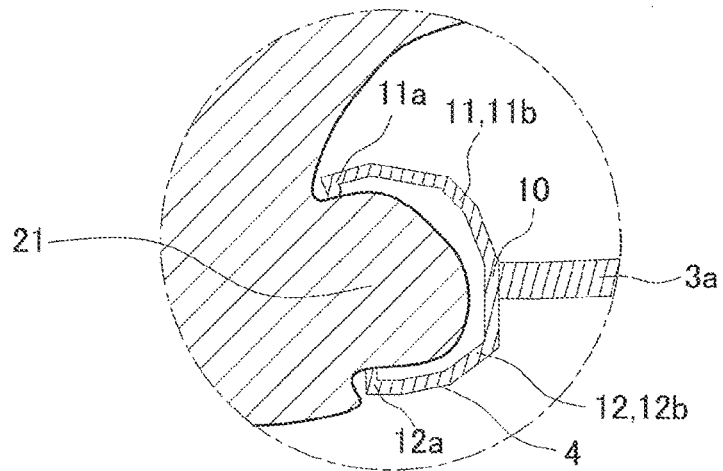
FIG. 9C is a cross-sectional view showing Modification 3 of the hook portion (unit hook portion).

As shown in FIG. 9C, the end portion 11a may be formed as a folded-back portion obtained by folding downward the upward-extending upper portion 11. When the ciliary processes 21 are inserted into the internal region of the substantially-C-shaped unit hook portions 8 due to the folded-back portion, the folded-back portion serves as a barb and can prevent the ciliary processes 21 squeezed into the unit hook portions 8 from being detached therefrom. A folded-back portion may be provided to the end portion 12a. The substantially C shape is described as an example of the shape of each unit hook portion 8, but the shape of each unit hook portion 8 is not limited to the substantially C shape as long as the shape is a shape along the ciliary processes 21.

In the above embodiments and modifications, the disc-shaped lens 2 has been described as an example. However, in addition to the disc shape, various forms such as a bowl shape along a spherical surface or an elliptical plate shape may be adopted as the shape of the lens 2. The example in which the unit hook portions 8 are disposed adjacently at regular intervals around the axial line L as shown in FIG. 1C has been described. However, the intervals of the adjacent unit hook portions 8 may not be regular intervals. The same applies to the hook portions 4. In addition, the hook portions 4 may be continuously disposed around the axial line L, whereby the to-be-mounted object such as the lens 2 can be firmly held in the eye.

In the above embodiments and modifications, the sharply-bending upper bent portions 11b and lower bend portions 12b have been described as an example. However, the upper bent portions 11b and lower bend portions 12b may be formed as upper bent portions and lower bent portions that are bent in a curved manner. Accordingly, it is possible to improve the degree of close contact between the unit hook portion and the ciliary processes 21.

In the above embodiments and modifications, the example in which each hook portion is formed in a comb shape, a net shape, or a hoe shape has been described. However, each hook portion may be formed in a band shape covering a portion or the entirety of the ciliary processes 21 along the outer surfaces of the ciliary processes 21. In addition, each hook portion may be formed in a palisaded shape. The base portions 21a of the ciliary processes 21, serving as base points, from which the hook portions 4 extend along the outer surfaces of the ciliary processes 21 are not limited to the bases of the ciliary processes 21 as long as the hook portions 4 can be hooked or fitted to the ciliary processes 21. The base portions may be, for example, middle portions located between the bases and the anterior ends of the ciliary processes 21. The same applies to the terminations of the hook portions 4 extending along the ciliary processes.

Although the embodiments of the invention have been described above, the invention is not limited to the specific description thereof, and the illustrated configurations, processes, and the like can be combined as appropriate within a range where there is no technical contradiction, to practice the invention, or a certain element or process can be substituted with a known form to practice the invention.

The above description has been given on the premise that the ciliary processes 21 move obliquely upward as shown in FIG. 3D in response to relaxation/contraction of the ciliary body 20. However, according to the finding by the inventors, the ciliary processes 21 may possibly move laterally toward the visual axis C in FIG. 3D in response to relaxation/contraction of the ciliary body 20. In this case, the hook portions 4, 104, 204, 304, or 404 (hereinafter, referred to as "hook portions 4 or the like") attached to the ciliary processes 21 move in conjunction with the ciliary processes 21 moving laterally toward the visual axis C.

By the hook portions 4 or the like moving laterally, the bent portions 7 (see FIG. 2B) are pressed toward the visual axis C, the one end portion 5 of each leg 3*a* is changed into an attitude in which the one end portion 5 is nearly orthogonal to the lens 2, and the lens 2 is pressed upward. Then, when the hook portions 4 or the like return to the original positions, the lens 2 moves downward and returns to the original position. By moving the lens 2 up and down in this manner, the distance between the lens 2 and a visual target an image of which is to be formed on the retina by the lens 2 may be changed.

DESCRIPTION OF THE REFERENCE CHARACTERS 1 intraocular lens (intraocularly-mounted object)
2 lens (to-be-mounted object)
3 leg portion
3*a* leg
4 hook portion
5 one end portion
6 other end portion
7 bent portion
8 unit hook portion
9 connection portion
10 intermediate portion
11 upper portion
12 lower portion
13 eye
14 crystalline lens
15 anterior capsule
16 posterior capsule
17 cornea
20 ciliary body
21 ciliary process
22 ciliary zonule

The invention claimed is:

1. An intraocularly-mounted object configured to be placed inside an eye on an outer surface of a base portion of a ciliary process which projects toward a visual axis of the eye, comprising:
   an intraocular lens having an axial line;
   a predetermined number of leg portions radially extending from the intraocular lens, each of the leg portions having a distal end and a proximal end connected to the lens;
   a predetermined number of hook portions each connected to the distal end of a corresponding one of the leg portions, the hook portions each having a substantially C claw-like shape defining a ciliary process contacting-surface formed by an upper portion, a lower portion and an intermediate portion between the upper portion and the lower portion, the upper portion and the lower portion projecting away from the axial line while the intermediate portion projecting toward the axial line so as to form a space for accepting the base portion of the ciliary process as the axial line is being aligned with the visual axis when the intraocularly-mounted object is placed in the eye,
   wherein each of the hook portions further comprises:
      a plurality of unit hook portions disposed adjacently in an arc at a predetermined intervals about the axial line; and
      at least one connection portion that connects the plurality of unit hook portions together.

2. The intraocularly-mounted object according to claim 1, wherein the least one connection portion connects the plurality of adjacent unit hook portions in a comb shape.

3. The intraocularly-mounted object according to claim 1, wherein the least one connection portion connects the plurality of adjacent unit hook portions in a net shape.

4. The intraocularly-mounted object according to claim 1, wherein a distance D1 is a distance along the axial line between a first predetermined point on the upper portion and a second predetermined point on the lower portion wherein the distance D1 ranges from 1 mm to 4 mm.

5. The intraocularly-mounted object according to claim 4, wherein a distance D2 is a distance perpendicular to the axial line between a third predetermined point on the intermediate portion and a line connecting the first predetermined point on the upper portion and the second predetermined point on the lower portion, wherein the distance D2 ranges from 0.5 mm to 2 mm.

6. The intraocularly-mounted object according to claim 5, wherein a ratio between the distance D1 and the distance D2 ranges from 0.5 to 8.

7. The intraocularly-mounted object according to claim 1, wherein an angle ranges from 1 degree to 9 degrees between adjacent two of the unit hook portions about the axial line.

* * * * *